(12) United States Patent
Leduc

(10) Patent No.: US 7,409,044 B2
(45) Date of Patent: Aug. 5, 2008

(54) EMERGENCY CALL SYSTEM AND DEVICE

(75) Inventor: Michel Leduc, Trets (FR)

(73) Assignee: GEMPLUS, Gemenos (FR)

( * ) Notice: Subject to any disclaimer, the term of this patent is extended or adjusted under 35 U.S.C. 154(b) by 1108 days.

(21) Appl. No.: 10/333,407

(22) PCT Filed: Jul. 19, 2001

(86) PCT No.: PCT/FR01/02356

§ 371 (c)(1),
(2), (4) Date: Jan. 21, 2003

(87) PCT Pub. No.: WO02/09409

PCT Pub. Date: Jan. 31, 2002

(65) Prior Publication Data
US 2004/0024706 A1 Feb. 5, 2004

(30) Foreign Application Priority Data
Jul. 21, 2000 (FR) .................................. 00 09627

(51) Int. Cl.
H04M 11/00 (2006.01)
(52) U.S. Cl. ..................... 379/37; 379/106.02

(58) Field of Classification Search ............. 379/37–40, 379/106.02; 455/404.1
See application file for complete search history.

(56) References Cited

U.S. PATENT DOCUMENTS

| 5,291,399 | A |   | 3/1994 | Chaco |   |
|---|---|---|---|---|---|
| 5,455,851 | A | * | 10/1995 | Chaco et al. ................... | 379/38 |
| 5,719,929 | A | * | 2/1998 | Menard ........................ | 379/40 |
| 6,671,351 | B2 | * | 12/2003 | Menard et al. ................ | 379/45 |
| 6,799,031 | B1 | * | 9/2004 | Lewiner et al. ................ | 379/40 |
| 6,807,564 | B1 | * | 10/2004 | Zellner et al. ................. | 379/37 |
| 7,127,300 | B2 | * | 10/2006 | Mazar et al. .................. | 607/60 |
| 2001/0037220 | A1 | * | 11/2001 | Merry et al. ................... | 705/3 |

FOREIGN PATENT DOCUMENTS

WO 96/06409 2/1996
WO 98/50873 11/1998

* cited by examiner

Primary Examiner—Stella L Woo
(74) Attorney, Agent, or Firm—Buchanan Ingersoll & Rooney PC

(57) ABSTRACT

An emergency call system includes an emergency call device capable of accessing at least a wireless telecommunication network by means of a communication apparatus. A server processes the emergency call coming from an emergency call device via the communication apparatus. The invention is applicable to emergency call systems in case of health accidents, assaults, accidents and the like. The emergency call device can be a smart card.

13 Claims, 1 Drawing Sheet

Call button 20
Data display 28
Sensor 30

EMERGENCY CALL SYSTEM AND DEVICE

This disclosure is based upon French Application No. 00/09627, filed on Jul. 21, 2000 and International Application No. PCT/FR01/02356, filed Jul. 19, 2001, the contents of which are incorporated herein by reference.

BACKGROUND OF THE INVENTION

The invention relates to emergency call systems and devices which enable the bearers of these emergency call devices to inform an emergency call centre of the occurrence of an event which requires urgent processing.

These systems and devices are used, for example, by elderly people in the event of a health problem or a problem of protection against theft and assaults. To that end, the elderly person is equipped with a fixed telephone and a device for controlling the telephone so as to automatically generate a telephone call by means of the fixed telephone to the emergency call receiving and processing centre. This device can be a simple button on the fixed telephone or an object carried by the elderly person communicating by radiofrequency with the fixed telephone.

There also exist, on the telephone networks, emergency call numbers limited to two or three digits in order to facilitate memorisation and dialling.

These systems and devices of the prior art have the following drawbacks:
- a reduced field of action since this is limited solely to the network to which the telephone handset is connected, for example the conventional telephone network, the GSM network, the Internet, etc.;
- a geographical area limited to the immediate vicinity of the telephone handset;
- authentication of the caller is carried out by means of the calling number, which is not error-free, in particular in the case of erroneous or malicious calls;
- no information is transmitted as regards the personal and medical data of the caller;
- no information is transmitted as regards the biomedical data related to the emergency situation, in particular the blood pressure, heart rate, blood sugar level, etc.

SUMMARY OF THE INVENTION

One aim of the present invention is to implement a system for emergency calls by means of at least one emergency call device which does not have the aforementioned drawbacks of the systems of the prior art.

Another aim of the present invention is to implement an emergency call system and an emergency call device which make it possible to use all existing communication networks and, in particular, the one in the immediate vicinity of the emergency call device.

Another aim of the present invention is to implement an emergency call system and device which allow authentication of the caller.

Another aim of the present invention is to implement an emergency call system and device which allow the caller to provide permanent and/or real-time personal medical information. The invention therefore relates to an emergency call system, characterised in that it comprises:
- at least one emergency call device capable of accessing at least one wireless communication network comprising at least one communication appliance; and
- a server for processing the emergency call coming from the emergency call device by means of at least said communication appliance.

According to the invention, each emergency call device comprises:
- means of triggering the emergency call;
- communication means for automatically connecting to said communication network after the triggering of the emergency call and communicating with said communication appliance of the network;
- means for recording the procedure for accessing the emergency call processing server by means of the communication appliance; and
- means for automatically using the procedure for accessing the emergency call processing server via the communication appliance.

It also comprises a sensor of certain biometric data of the caller with a view to the authentication of said caller by comparison with previously recorded biometric data.

The emergency call device furthermore comprises means for recording personal and medical information of the caller and transmitting it, on authorised request, to the emergency call processing server.

It also comprises, furthermore, means for receiving information coming from medical sensors disposed on the caller and transmitting it, on request, to the emergency call processing server. Encryption/decryption means can be provided for maintaining the confidentiality of certain transmitted information.

BRIEF DESCRIPTION OF THE DRAWINGS

Other characteristics and advantages of the present invention will emerge from a reading of the following description of one particular example embodiment, said description being produced with the accompanying drawings in which.

DETAILED DESCRIPTION

Figure 1:
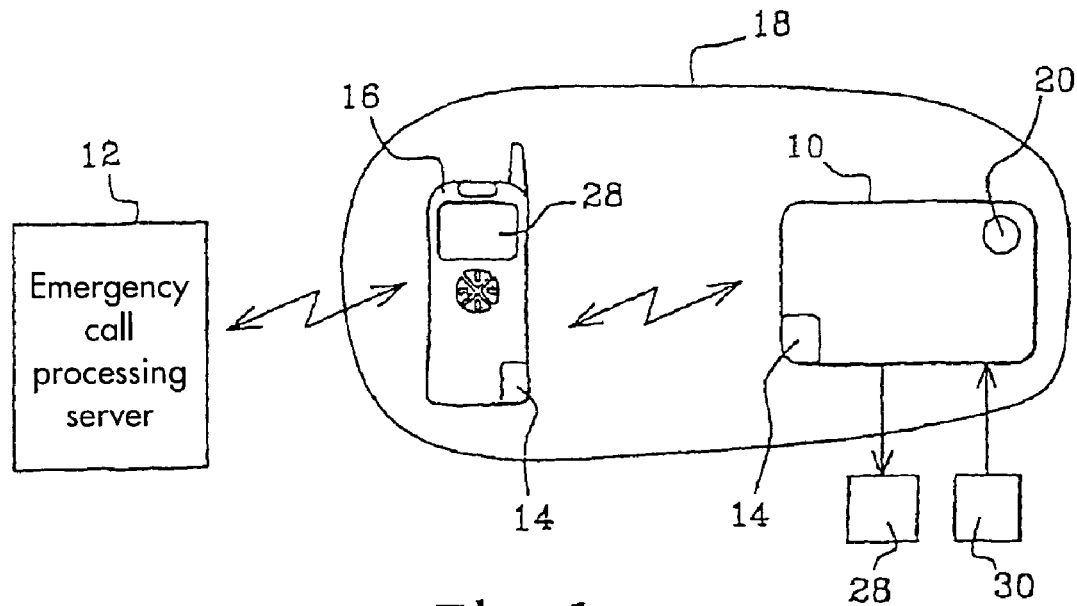
FIG. 1 is a diagram of an emergency call system according to the invention.

The emergency call system according to the invention comprises at least one emergency call device such as that referenced 10 and an emergency call processing server referenced 12.

The emergency call device 10 is of the contactless smart card type which is equipped with communication means 14 enabling it to connect and communicate with appliances of a wireless communication network 18 having the same communication means 14. Such a wireless communication network and the communication means 14 are known and described in the specialist literature. They operate at radiofrequency like the Bluetooth system for example, defined by the European documents ETS 300-328 and ETS 300-339 or by infrared like the IRDA system.

Thus, the emergency call device 10 can connect and communicate with a portable type communication appliance 16 which is equipped with communication means 14. It is this appliance 16 which can communicate with the server 12 according to the conventional telephone networks as opposed to the local network 18.

Figure 2:
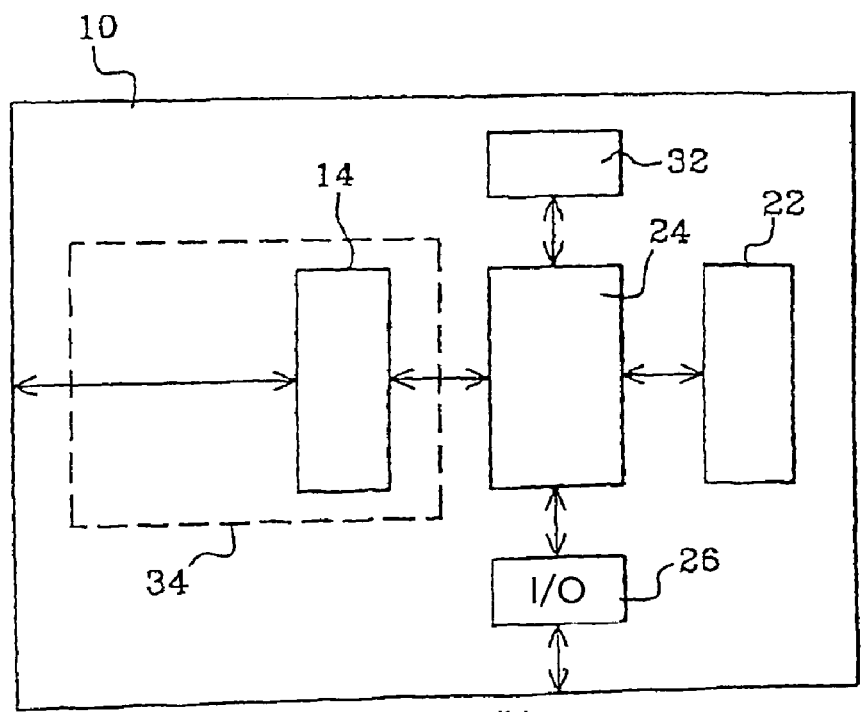
FIG. 2 is a functional diagram of an emergency call device according to the invention.

Besides the communication means 14, the emergency call device 10 comprises (FIG. 2):

means 20 for triggering an emergency call such as a button;

means 22 such as memories for recording the procedures for accessing the server 12, each procedure varying according to the type of local communication network 18 and the type of communication appliance 16;

means 24 such as a microprocessor for selecting the procedure for appropriate access to the server 12 in order to use it automatically.

The memories 22 record, besides the access procedures, personal and medical information, relating to the registered bearer of the card. Amongst this personal information, there is information for identifying the caller such as an access code but also biometric information which makes it possible to authenticate the bearer by comparing it with biometric information measured by means of the call button 20 which is at the same time a biometric sensor.

This measured biometric information is processed by the microprocessor 24 via an input/output circuit 26.

This input/output circuit 26 is also provided for connecting the microprocessor 24 to a device 28 for displaying the personal and medical information of the bearer as well as to medical sensors 30 disposed on the body of the bearer for measuring the blood pressure, heart rate, blood sugar level, etc. This medical information measured by the medical sensors 30 is transmitted to the server 12.

The memories 22 are also provided for recording information or instructions received from the server 12, this information then being communicated to the bearer or to any other person in the vicinity of the bearer.

In order to maintain the confidentiality of the transmitted information, the emergency call device furthermore comprises encryption/decryption means 32 which are used on command from the microprocessor 24.

The emergency call device 10 is preferably equipped with as many communication means 14 as types of local network (Bluetooth, IRDA, etc.), so as to be able to connect and communicate with a maximum number of communication appliances situated in the immediate surroundings of the call device. This is the meaning of the rectangle in dashed lines 34 for indicating that there are a number of means 14.

The operation of the system according to the invention is then as follows.

When the bearer of the emergency call device presses the button 20 for a time greater than a few seconds, it triggers the bearer authentication procedure using the biometric data such as a fingerprint. To that end, the image of the fingerprint originating from the sensor is compared with the reference image contained in the memories 22. If the comparison is positive, the emergency call procedure is initiated. This consists first in searching for a local communication network 18 comprising a communication appliance 16.

If the comparison is negative, the call procedure is not initiated. This authentication makes it possible to avoid calls by unauthorised persons.

As soon as the communication is established, the emergency call device initiates the procedure for accessing the server 12 via the communication appliance 16. When the link is established, the emergency call device carries out a mutual identification of the bearer and the server to which it is connected in order to validate the call. The bearer identification information is transmitted to the server so as on the one hand to validate the call and on the other hand to make sure that the intervention is possible.

If necessary, the personal and/or medical information is transmitted by the emergency call device after verification of the access rights of the server.

Furthermore, the information provided by the sensors 30 will be transmitted to the server after request therefrom and verification of its rights of access to this type of information.

The server 12 can send information to the emergency call device 10 and the latter can display it via the display circuit 28.

The emergency call system and device according to the invention has the following advantages:

it is not tied to a particular communication link, for example a telephone line, with the result that the call can use a number of types of communication link;

it is not tied to a given geographical location, which makes it possible to use it in all locations;

authentication of the caller is carried out from the very beginning of the call, which avoids false calls;

it allows information exchanges in both directions, encrypted or not, between the server and the user;

these information exchanges are under the control of the user through the use of access rights.

The invention claimed is:

1. A device for emergency calls to an emergency call processing server, said device comprising a smart card having a microprocessor, an emergency call triggering device, at least one contactless communication interface to access at least one communication appliance of a wireless communication network, and a memory containing procedures for causing said microprocessor to communicate with the communication appliance via said interface to access the server via the wireless communication network.

2. An emergency call device according to claim 1, wherein the emergency call triggering device is a biometric sensor, and the microprocessor compares sensed biometric data with reference biometric data contained in the memory before triggering a call.

3. An emergency call device according to claim 1, wherein said memory contains personal and/or medical information relating to the bearer, for transmission to the emergency call processing server.

4. An emergency call device according to claim 1, further comprising an input/output interface for connecting to at least one sensor which provides medical measurement values, for transmission to the processing server.

5. An emergency call device according to claim 1, wherein the memory further contains information received from the server, and wherein said device further comprises means for displaying said information.

6. An emergency call device according to claim 1, wherein said device further comprises means for encrypting/decrypting the information transmitted to the server or received from the server.

7. An emergency call system, comprising at least one emergency call device according to claim 1 and a server for processing an emergency call from the emergency call device by means of said communication appliance.

8. An emergency call system, comprising:

a smart card having:

a microprocessor;

a call triggering device;

at least one contactless communication interface; and a memory storing a procedure for causing said microprocessor to establish communication with a communication appliance in response to actuation of said triggering device for accessing an emergency call processing server; and a wireless communication appliance having a wireless communication interface that enables said communication appliance to communicate with said smart card, said communication appliance being responsive to the establishment of communication with said smart card to communicate with said emergency call processing server via a wireless network and thereby enable said smart card to access said server.

9. The emergency call system of claim 8, wherein the call triggering device is a biometric sensor, and the microprocessor compares sensed biometric data with reference biometric data contained in the memory before triggering a call.

10. The emergency call system of claim 8, wherein said memory contains personal and/or medical information relating to the bearer, for transmission to the emergency call processing server.

11. The emergency call system of claim 8, further comprising an input/output interface for connecting to at least one sensor which provides medical measurement values, for transmission to the emergency call processing server.

12. The emergency call system of claim 8, wherein the memory further contains information received from the server, and wherein said smart card includes a display for displaying said information.

13. The emergency call system of claim 8, wherein said smart card includes a module for encrypting/decrypting the information transmitted to the server or received from the server.

* * * * *